United States Patent
Kalantar-Zadeh

(10) Patent No.: US 7,482,732 B2
(45) Date of Patent: Jan. 27, 2009

(54) LAYERED SURFACE ACOUSTIC WAVE SENSOR

(75) Inventor: Kourosh Kalantar-Zadeh, Melbourne (AU)

(73) Assignee: MNT Innovations Pty Ltd, Scoresby (AU)

(*) Notice: Subject to any disclaimer, the term of this patent is extended or adjusted under 35 U.S.C. 154(b) by 0 days.

(21) Appl. No.: 10/590,367

(22) PCT Filed: Feb. 25, 2005

(86) PCT No.: PCT/AU2005/000244

§ 371 (c)(1), (2), (4) Date: Oct. 10, 2006

(87) PCT Pub. No.: WO2005/083882

PCT Pub. Date: Sep. 9, 2005

(65) Prior Publication Data

US 2007/0241637 A1    Oct. 18, 2007

(30) Foreign Application Priority Data

Feb. 26, 2004  (AU)  ............................. 2004900942

(51) Int. Cl.
*H01L 41/04* (2006.01)
(52) U.S. Cl. .............................. 310/323.21; 73/514.34; 324/633
(58) Field of Classification Search ............ 310/323.21; 73/514.34; 324/633
See application file for complete search history.

(56) References Cited

U.S. PATENT DOCUMENTS

| 3,979,697 A | | 9/1976 | Donahue |
| 4,025,954 A | * | 5/1977 | Bert ............................. 348/198 |
| 4,107,626 A | * | 8/1978 | Kiewit ........................... 331/65 |
| 4,361,026 A | * | 11/1982 | Muller et al. ............... 73/24.01 |
| 4,562,371 A | | 12/1985 | Asai et al. |
| 4,868,524 A | | 9/1989 | Costlow et al. |

(Continued)

FOREIGN PATENT DOCUMENTS

JP          09-093079          4/1997

(Continued)

OTHER PUBLICATIONS

Bill Drafts "Sensors-Oct. 2000-Acoustic Wave Technology Sensors", Retrieved from the Internet on Jun. 19, 2002: <URL:www:sensormag.com/articles/1000/68/main.stml> Whole article and in particular see chapter titled "Sensor Applications" and Figure 11.

*Primary Examiner*—J. A San Martin
(74) *Attorney, Agent, or Firm*—Connolly Bove Lodge & Hutz LLP

(57) ABSTRACT

A surface acoustic wave sensor which incorporates: a) a first layered SAW device consisting of a piezoelectric crystal such as lithium niobate or lithium tantalate with interdigital electrodes on its surface, and second piezoelectric layer such as zinc oxide over said interdigital electrodes b) a second layered SAW device consisting of a piezoelectric crystal with interdigital electrodes on its surface, a second piezoelectric layer over said interdigital electrodes and an analyte sensitive surface such as gold on said second piezoelectric layer c) both saw devices are fabricated on the same substrate d) reflectors are located adjacent the interdigital electrodes in each saw device to reduce the bandwidth of the device e) the resonator circuits of each saw sensor incorporate amplifiers which are dependent.

7 Claims, 12 Drawing Sheets

U.S. PATENT DOCUMENTS

| | | | |
|---|---|---|---|
| 5,012,668 A | 5/1991 | Haworth | |
| 5,117,146 A * | 5/1992 | Martin et al. | 310/313 R |
| 5,126,694 A | 6/1992 | Montress et al. | |
| 5,130,257 A | 7/1992 | Baer et al. | |
| 5,216,312 A | 6/1993 | Baer et al. | |
| 5,283,037 A * | 2/1994 | Baer et al. | 422/82.01 |
| 5,321,331 A | 6/1994 | Baer et al. | |
| 5,705,399 A | 1/1998 | Larue | |
| 5,817,922 A | 10/1998 | Rapp et al. | |
| 5,889,351 A * | 3/1999 | Okumura et al. | 310/321 |
| 6,122,954 A | 9/2000 | Bowers | |
| 6,378,370 B1 * | 4/2002 | Haskell et al. | 73/579 |
| 6,480,076 B2 | 11/2002 | Yip et al. | |
| 6,762,533 B2 * | 7/2004 | Iwamoto et al. | 310/313 B |
| 7,002,281 B2 * | 2/2006 | Andle | 310/313 B |
| 7,027,921 B2 * | 4/2006 | Kalantar-Zadeh et al. | 702/2 |
| 2003/0201694 A1 * | 10/2003 | Lu et al. | 310/313 A |
| 2006/0049714 A1 * | 3/2006 | Liu et al. | 310/313 R |
| 2007/0089525 A1 * | 4/2007 | Momose et al. | 73/753 |

FOREIGN PATENT DOCUMENTS

| | | |
|---|---|---|
| JP | 2000-261276 | 9/2000 |
| JP | 2000-312126 | 11/2000 |
| WO | 2002/095940 A1 | 11/2002 |

* cited by examiner

LAYERED SURFACE ACOUSTIC WAVE SENSOR

This application is the National Stage of International Application Ser. No. PCT/AU2005/000244 filed on Feb. 25, 2005; and this application claims priority of application Ser. No. 2004900942 filed in Australia on Feb. 26, 2004 under 35 U.S.C. § 119; the entire contents of all are hereby incorporated by reference.

This invention relates to improvements in Surface Acoustic Wave [SAW] devices and particularly layered SAW devices used as sensors.

BACKGROUND OF THE INVENTION

SAW devices are usually used in a closed loop with an amplifier to make an oscillator. There are patents which describes setting up a stable oscillator using a SAW device to generate clock pulses for electronic circuits. U.S. Pat. No. 3,979,697 discloses an oscillator in which the "tank circuit" or feedback element is a surface acoustic wave (SAW) bandpass filter (delay line). U.S. Pat. No. 4,868,524 discloses an RF circuit to generate a stable carrier signal using a Voltage Controlled Saw Oscillator. U.S. Pat. No. 5,126,694 discloses A SAW stabilized oscillator includes a phase locking circuit which is phase locked to a lower frequency reference signal having an odd order difference with respect to the fundamental frequency of the SAW oscillator.

SAW devices have been used as sensors in liquid and gaseous environments. U.S. Pat. No. 4,562,371 discloses a SAW device comprising a ZnO piezo layer on a cut crystalline silicon substrate that propagates Rayleigh waves.

The surface acoustic waves polarizes in 3 directions and can be classified as longitudinal wave motion, Normal waves or shear horizontal waves. A class of shear horizontal [SH] waves are called Love waves which are propagated in layered devices that concentrate the wave energy in a highly confined region near to the surface.

Rayleigh wave sensors have been useful in gaseous environments but they are not suitable for liquid environments because the surface-normal displacement causes strong radiative loss into the liquid. For sensing in liquids shear horizontal [SH] polarised wave modes are preferred since the particle displacement is parallel to the device surface and normal to the direction of propagation. This allows a wave to propagate in contact with a liquid without coupling excessive acoustic energy into the liquid. However the SH wave is distributed through the substrate and therefore does not have the same sensitivity as the SAW. For increased sensitivity Love waves which are SH-polarised guided surface waves may be used. The waves propagate in a layered structure consisting of a piezoelectric substrate and a guiding layer which couples the elastic waves generated in the substrate to the near surface. They are extremely sensitive to surface perturbations due to the energy confinement to the near surface. By observing the magnitude of perturbations it is possible to measure the strength of the interaction. The interactions may be caused by mass density, elastic stiffness, liquid viscosity, electric and dielectric properties. The more sensitive is the device the smaller the quantities that can be measured.

U.S. Pat. Nos. 5,130,257, 5,216,312, 5,283,037 and 5,321,331 disclose love mode SAW sensors used in liquid environments. The love waves are produced by cutting the piezo electric material such as lithium niobate, lithium tantalate or quartz to couple energy from the interdigital transducers [IDT's] of the SAW device into shear transverse or love waves that enable the wave energy to be trapped at the substrate surface.

U.S. Pat. No. 5,705,399 discloses a SAW sensor for liquid environments having an AT cut quartz piezo substrate with electrodes connected to a first side in contact with a liquid and a second side that is not in contact. The sensor may be used to detect biological species such as antigens.

WO02/095940 discloses a love mode SAW sensor using a piezo layer of ZnO on a piezo electric quartz crystal.

To improve the sensitivity of sensors the stability of the frequency of the device needs to be addressed. U.S. Pat. No. 6,122,954 discloses a SAW sensor with a resonant frequency range of 200 to 2000 MHz and a temperature control system.

It is an object of this invention to improve the reliability of SAW sensors and to optimise the operational performance of the sensors.

BRIEF DESCRIPTION OF THE INVENTION

To this end the present invention provides a surface acoustic wave sensor which incorporates
a) a first layered SAW device consisting of a piezoelectric crystal with interdigital electrodes on its surface, and second piezoelectric layer over said interdigital electrodes
b) a second layered SAW device consisting of a piezoelectric crystal with interdigital electrodes on its surface, a second piezoelectric layer over said interdigital electrodes and an analyte sensitive surface on said second piezoelectric layer
c) both SAW devices are fabricated on the same substrate
d) reflectors are located adjacent the interdigital electrodes in each saw device to reduce the bandwidth of the device
e) the resonator circuits of each saw sensor incorporate amplifiers which are dependent.

When the SAW device interacts with a target analytes the operating frequency changes. The change of operating frequency is proportional to the magnitude of the target analyte in the environment. The oscillation system needs to have a high Q and a stable frequency response.

By using the first layered SAW device as a reference sensor and fabricating them on the same substrate the effect of environmental noise can be reduced. By using reflectors to reduce the bandwidth the Q of the devices is increased.

Preferably the piezoelectric substrate is cut for propagation of Love mode waves and may be quartz crystal, lithium Niobate [$LiNbO_3$], lithium tantalate [$LiTaO_3$], langasite or langatite.

Preferably the second layer is a piezoelectric film such as layer is zinc oxide, AlN LiTaO3, LiTaO3 or quartz The second layer can be a non-piezoelectric which has a capability to confine the acoustic energy with itself such as silicon nitride, different types of metal oxides, polymers or metal compounds.

A preferred piezo substrate is 90° rotated ST-cut quartz crystal which has a propagation speed of 5000 m/s and the dominant wave is SSBW (Surface Skimming Bulk Wave) and has zero coupling to other modes. It is dominantly a Shear Horizontal (SH) bulk wave and has a low temperature coefficient. Its major disadvantage is a high insertion loss as it changes from SSBW to love mode. When a film material is deposited on the surface it should load the substrate which means the speed of propagation in the film is less than in the substrate. In this case the mode of propagation changes to Love mode. When metal oxides films are deposited on the substrate the insertion loss is decreased as the mode of operation changes from SSBW to Love mode. Its main advantage is a lower insertion loss as it decreases from SSBW to Love mode.

Other suitable substrates are the substrates that allow the generation of leaky SAWs. These include LST quartz, 64 YX-LiNbO$_3$, 41 YX-LiNbO$_3$ and 36 YX-LiTaO3 substrates.

Other substrates cuts, which allow propagation of Rayleigh or other type of waves, can be used for gas sensing applications. Again addition of an acoustic confining layer increases sensitivity of the device.

Substrates that we have employed and tested are: ST cut quartz, XY and Yz LiNBO$_3$, 128 X LiNbO$_3$, 110 Bismuth germanium oxide, different cuts of LiTaO$_3$, GaAs, langatite and langasite.

Different types of second layers are used: metal compounds, metal oxides, metal nitrides, binary compounds, polymers, nano-particle compounds and amorphous materials.

One of the simplest, most economic and most reliable methods of operating a SAW device is to place it in a feed-back-loop. Implementing this, the system oscillates at a frequency, which is a function of the width of the finger pairs of the SAW device pattern and the speed of propagation of the delay line. A change in the operational frequency of the system is resulted from the change in the acoustic wave propagation speed which itself is changed via the interaction with an analyte.

A biologically sensitive layer is deposited on the second piezo layer of the second SAW device to interact with the appropriate biochemical components to be detected. A gold film may be deposited on the surface. Gold interacts with high affinity to proteins. It can be used with specific antibodies for antigen detection. This deposit can be made on a porous surface as well as a smooth surface. A simple SAW oscillator may contain and amplifier, a SAW device, an output coupler and a means of setting loop phase shift for instance via a length of a coax cable. The saturation of the loop amplifier provides the gain compression. A very important aspect in the design and implementation of a SAW sensing system, which operates based on an oscillator, is the stability of the frequency. Different types of phenomenon may cause a frequency deviations from the base frequency in a sensing system. They can be categorized as follow:

1—Random deviations generated by random noise
2—Drift as a constant frequency shift. This can be a short term or a long term drift
3—Electromagnetic effects. Although shielding dramatically reduces this effect but affinity of any metal or material with high permittivity to the system may generate a frequency change
4—Noise due to the mechanical component of the system such as pumps and injection of the analyte
5—Frequency changes caused by warming up of the electronic circuits and random noise generated in them The frequency stability for a SAW oscillation system is divided into systematic and random categories:

1. Systematic are the predictable effects
2. Random effects are different regarding prediction and spectral densities than systematic effects Random noises are generally difficult to quantify, as they are not a state of frequency which is changing at a specific time period. Furthermore, random noise value strongly depends on the number of samples and the total length of measurement. For the study of random noise, the spectra of the frequency are normally the most common parameters to inspect.

Among random noises, the parameter which has the most important effect on oscillation frequency, is the change in temperature. It has effect both on the SAW device and on the electronic components of the loop's amplifier.

The characteristics of the temperature coefficient of frequency is largely dependant on the cut of the crystal. Generally, the frequency change generated by the temperature change can be dramatically suppressed by employing a dual delay line device and looking at the difference of the two oscillations.

DETAILED DESCRIPTION OF INVENTION

The present invention adds to the proposals disclosed in WO 02/095940 the content of which is incorporated herein by reference.

This invention provides piezoelectric layers on piezoelectric substrates. The Substrate's cut belongs to a class of crystal cuts that support Surface Skimming Bulk Wave (SSBW) and leaky wave for liquid sensing applications and other cuts for gas sensing applications. The layers are of different of piezoelectric materials that can be deposited as a highly directional film on the substrate, which let acoustic waves propagate onto its environment. Speed of propagation of acoustic wave in the layers must be less than the substrate to support Love mode of propagation, otherwise it allows other modes of propagation as well.

Figure 1:
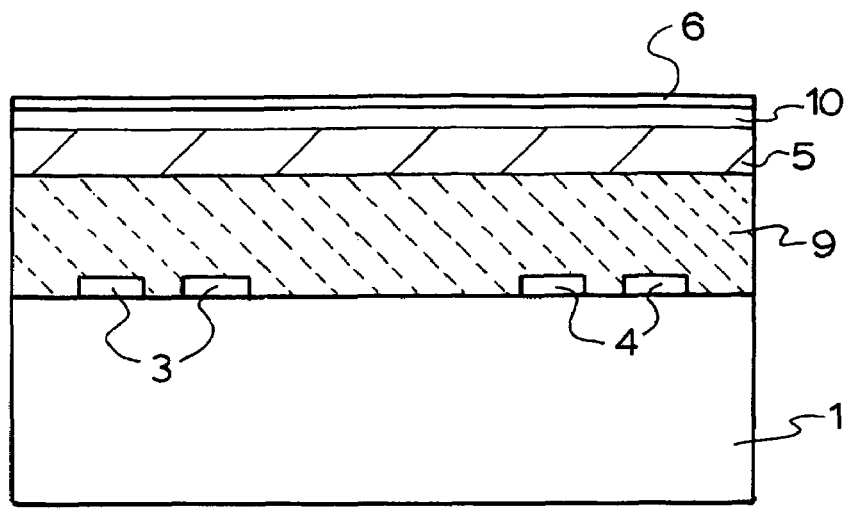
FIG. 1 is a cross section of a saw sensor to which the invention is applicable.

In FIG. 1 a first wave generating transducer 3 and a first receiving transducer 4 are fabricated onto the surface of a piezoelectric substrate 1. The transducers 3 and 4 are any suitable interdigital transducer used in SAW devices. The wave transmitting layer 5, a piezoelectric layer, is fabricated onto the substrate 1 such that the transducers 3 and 4 lie between the substrate 1 and the layer 5.

A sensing layer 6 is deposited on to the wave propagation layer 5 to form a surface which is physically, chemically or biologically active, selectively to agents in the liquid or gaseous media to which the surface 6 is exposed. The surface may be treated to detect any biological target. For quality control in food production the surface can be treated to detect quantitatively the presence of *Salmonella, E Coli,* or other enteric pathogens. For environmental monitoring pathogens such as *legionella* can be detected.

The transitional layer 9 is preferably an acoustically sensitive layer such as $SiO_2$ which increases the velocity shift and as a result increases the electromechanical coupling factor. The transition layer 9 lies between the wave transmitting layer 5 and the substrate 1 so that the distance between the first IDT and layer 5 is increased to facilitate a higher coupling coefficient and reduce the acoustic wave transmission energy loss which otherwise occur. The protective layer 10 lies between the sensing layer 6 and the piezo layer 5 to protect layer 5 from damage. The protective layer 10 may be $SiO_2$, other metal oxides, metal compounds or polymers.

Figure 2:
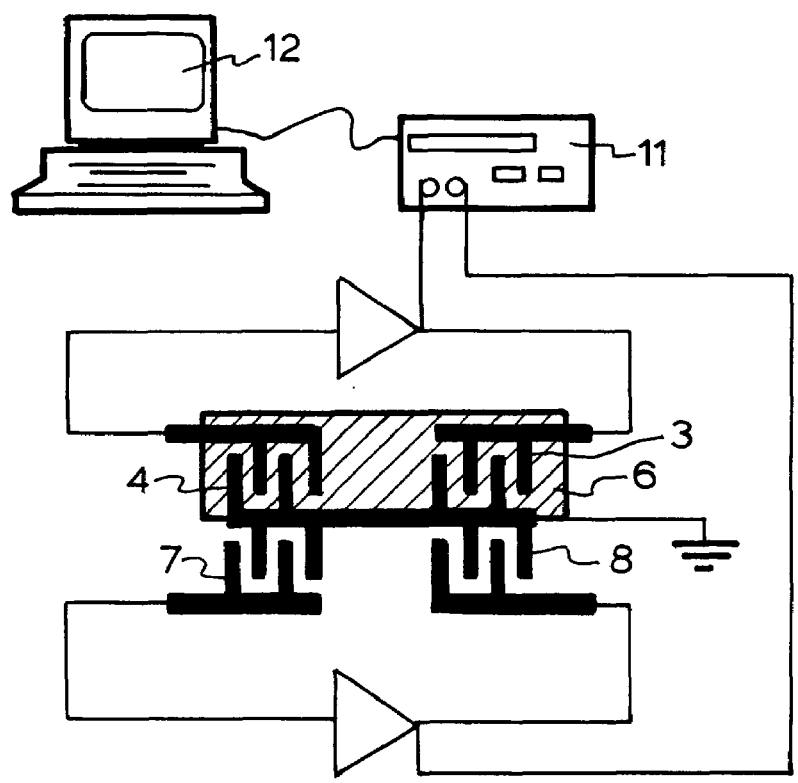
FIG. 2 is a schematic illustration of a preferred sensor and analyser of this invention.

In FIG. 2 the SAW device of this invention is shown in a detector device.

In FIG. 2 second wave generating transducer 7 and a second receiving transducer 8 above the substrate layer and below the wave transmitting layer and near the first generating transducers 3 and receiving transducers 4. Both sets of transducers are located on the same substrate. No sensing layer is located above the second set of transducers 7 and 8 so that they can function as a reference sensor.

A frequency counter 11 determines frequency of the output signals and a computing device 12 calculates the concentration of the detectable components in the liquid or gaseous media. The output from the first receiver transducer 4 contains the sensing signal which is a consequence of the interaction between the sensing layer and the target molecules. The output from the second receiving transducer 8 contains only the operational characteristics of the sensing device because thee is no sensing layer 6 above it. This enables the analyser to compute accurately a signal indicative of the concentration of the target molecule.

There are many parameters which effects the long term stability. Generally a final bake of the device makes a SAW device more stable. It is believed that the diffusion of metal into crystal is reduced in time with such a bake. This bake may generate a saturated diffusion level which reduces the room temperature diffusion.

The spectral density of frequency fluctuations S(f) is the magnitude of the mean square frequency fluctuation in a 1 Hz bandwidth. Another parameter used for quantifying random-frequency fluctuations is Allan variance. Allan parameter is the average value of one half of the square of the fractional change in frequency between two adjacent frequency measurements.

The issue of frequency deviation for the SAW sensors has been investigated. The differences for a SAW sensing system are as follow:
1—The system is in touch with an analyte. This analyte can be either gas or liquid. Contact with such materials may generate extra noise in the system. It results in more unpredictable behaviour of the system.
2—Generally a layered SAW device is used for liquid sensing applications. Most of the available studies so far are conducted for blank SAW devices.

Even for a blank device, the source of the frequency noise in SAW oscillators is not generally well understood. Contact with different analytes dramatically increases the complexity of the system.

In this invenstion the following methods were employed to reduce noise of the system and increase the frequency stability of the oscillation frequency:

1. Adding Gratings Between Transducers

Layered SAW devices are fabricated on to a crystal cut that allows the propagation of surface transverse wave (STW) (Leaky SAW and SSBW are in STW family). STW devices have:

Low device loss
High intrinsic Q
Low 1/f noise and
low vibration sensitivity

Currently, STW based resonators are widely used in modern communication and wireless remote sensing, weapon guiding systems.

By the deposition of a guiding film a layered SAW device is fabricated. The way to move to fabrication of a stable sensor is to design a high Q SH resonator.

The SH-type acoustic waves are excited by means of IDTs in a direction perpendicular to X-axis on selected temperature compensated rotated Y-orientation on the piezoelectric substrate. If IDTs are separated by a free surface from each other then SH-wave is a SSBW (surface skimming bulk wave) or leaky wave. For these modes of propagations the power is radiate into the bulk of the crystal, which increases the insertion loss. If a metal strip grating with a period equal to that of the IDTs is depostited between IDTs it slows down the SSBW and leaky waves and changed them to STW. The wave energy is confined onto the surface and does not dissipate into the bulk of the device.

In this invention the grating may be patterned either in between the guiding layers or on the surface of the SAW sensors. In both cases the insertion losses are decreased more than 15 dB.

2. Optimising Material Choice (For Example, the Use of Zinc Oxide)

Combination of different materials as the guiding layers and the substrate play a significant role in designing the sensitivity of the device. A layer with the shear horizontal speed of propagation less than that of the substrate usually confines the energy of acoustic waves into the layer. This near the surface energy increases the penetration of acoustic waves into the sensitive layer and target analytes. As a result, increasing the sensitivity of the device.

SAW wafers that allow the propagation of SSBW or leaky wave have to be employed for the fabrications of such devices. The guiding layers can be piezoelectric materials such as ZnO or non-piezoelectric materials such as $SiO_2$ and $Si_3N_4$.

3. The Number of Reflectors

Adding Reflectors reduces the bandwidth in a SAW device. This will increase the Q of the device, which has a dramatic effect on the signal to noise ratio of the operating system. Adding reflectors decreases the bandwidth of the device. Adding more than 50 reflectors for SAW devices based on LiTaO3 and LiNbO3 substrates have increased the Q of the devices up to one order of magnitude. For ST-cut quartz based devices, more than 150 reflectors are required but it increases the Q of the device up to 15 times.

4. Changing the Q of the Device by Changing the Cavity Length

Cavity length increases the Q of the device. For a better frequency stability the delay line should have a long delay time as possible. To ensure that only one frequency can satisfy the oscillation conditions at any given time, the combined length of the two transducers should be approximately no less than 90 percent of the centre-to-centre distance of the two transducers. The number of fingers in each transducers may be limited to approximately 120. Additional fingers can be used to achieve lower insertion loss, but this increases the undesirable influence of metal on turnover temperature and triple transit reflections.

A number of factors, such as propagation loss, physical size and phase error between groups of fingers contribute to limiting the length of the SAW transducer. At 400 MHz and achievable delay time for a single-mode delay line is about 4μ seconds.

Another advantage of large cavity size is that it increases the power handling capability of the resonator.

5. Fabricate both Devices (the Reference and the Sensor) on the Same Substrate.

This will dramatically decrease the environmental effects. Noises have generally the same effect on both sensor and reference oscillation frequencies and shift them with an equal magnitude. Substraction of these two frequency suppress the effect of environmental noise on the system.

6. Employing Dependant Amplifiers

The reference and sensor are better to be run by dependant amplifiers. The inventors have used arrays of transistors to reduce the effect of temperature on is the gain of the transistors and the environmental noise. When transistors are fabricated onto the same substrates then they show the same change in their gain, specially as temperature drifts.

Though the SAW device has by far the largest delay time of all oscillator components the other components play a significant role in the frequency stability of the oscillator.

In comparison to BAW resonators, SAW devices have one or two order of magnitude lower Q, as a result the influence of frequency stability of electronics is greater. To reduce the effect of stability of loop amplifier should have a large bandwidth. Employment of a negative feedback may help. It is also convenient to use a 50 ohm environment.

The best performance is obtained if bipolar silicon transistors are used as they give lower flicker noise than FETs. Their performance should not be sensitive to a source or load which is not exactly 50 ohm as in most cases SAW devices show different impedance than that of what they are designed for.

7. Optimising the Aperture Size

Aperture size has an important role when the sensor is operating in contact with a liquid. A typical delay line, in air, will have an insertion loss of approximately 20 dB if 120 fingers are used in each transducers and the acoustic aperture is approximately 200 wavelengths.

In contact with liquid the phase shift of the SAW device decreases. A large aperture compensates such a decrease.

8. Grooved Gratings

Grooved gratings usually give better frequency stability than metal grating since the only metal in the active acoustic area comes from the transducers. Despite such an advantage a larger cost may reduce the attractiveness of this method.

9. Device Packaging and Sensitivity to Vibration

The long term frequency stability related to the effect of analyte onto the surface of the SAW device. Ultra clean liquid is required when test for the long term SAW stability is tested. Otherwise a continuous drift is observed.

The vibration sensitivity is strongly dependant on the details of how the SAW device is mounted and packaged. Although normally the magnitude of vibration is small compared to temperature effects and long term drifts. Change in pressure of the liquid cell has a significant effect on the device. Even the pressure can be changed by small drops of liquid trickling from the outlet of a liquid delivery system.

Figure 3:
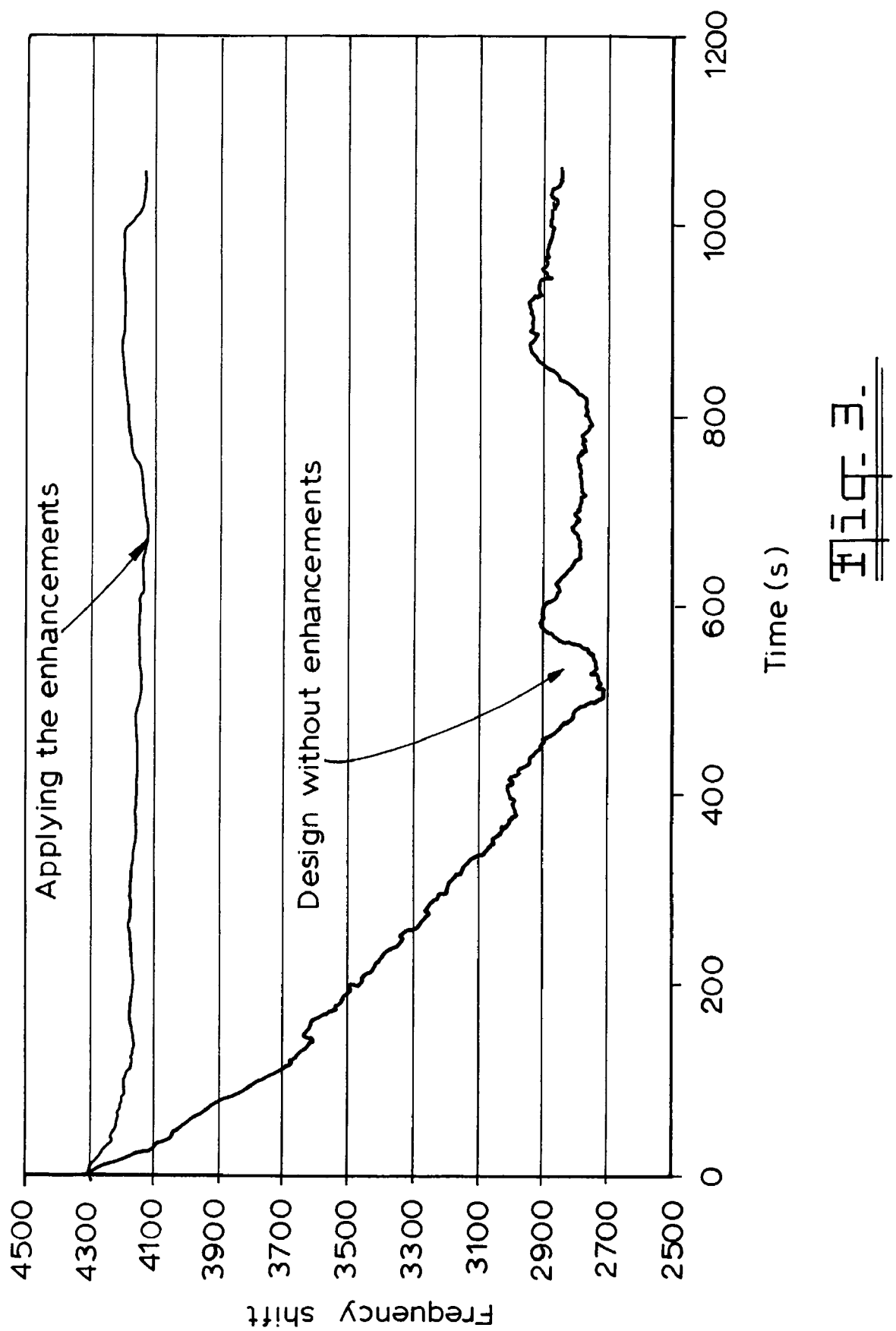
FIG. 3 illustrates the frequency shift performance of the invention.
Figure 4:
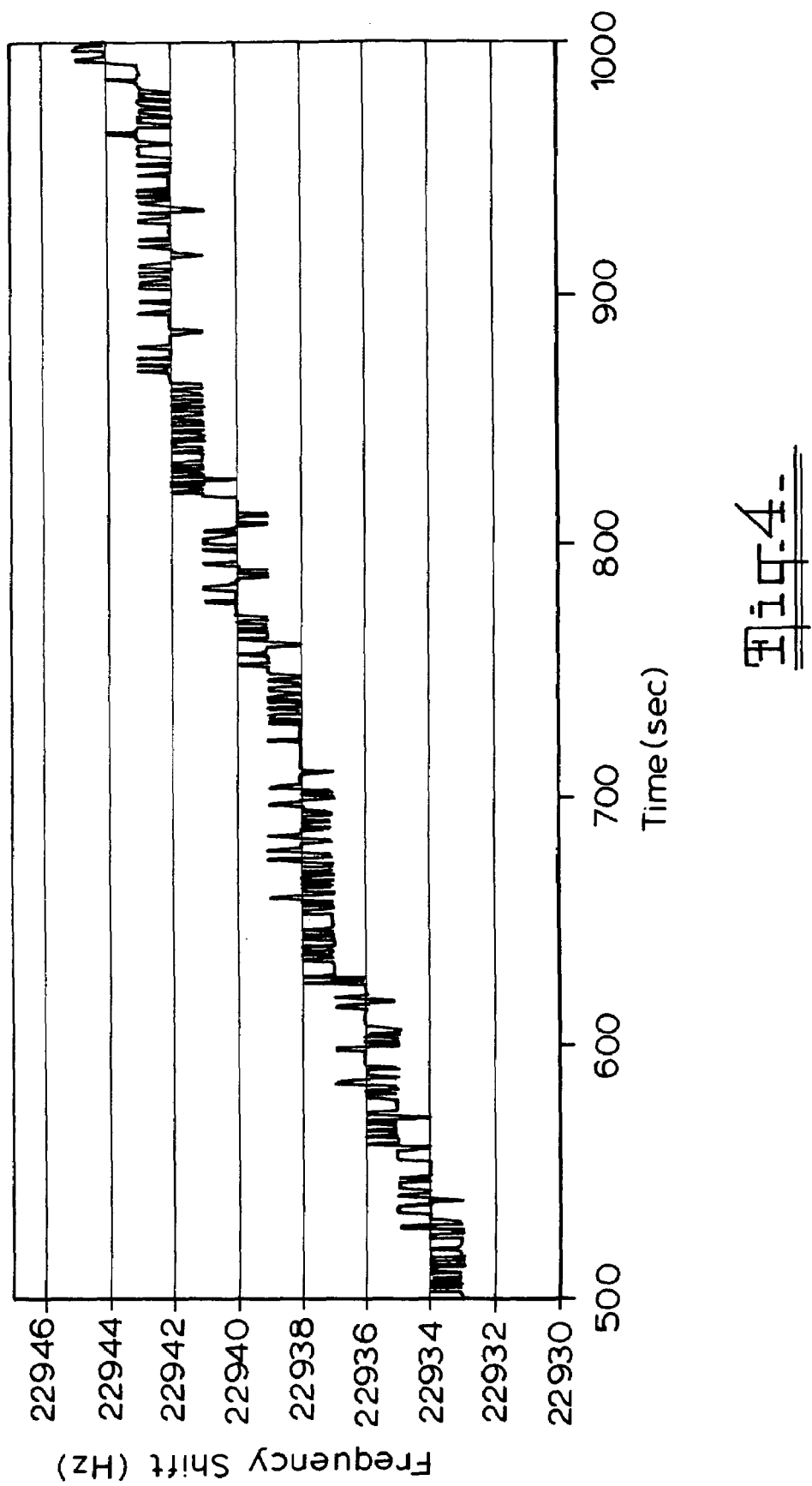
FIG. 4 illustrates the random noise of a SAW device of the invention.

The behaviour of the sensor of this invention is shown graphically in FIGS. 3 to 9. FIG. 3 shows the warming up of a SAW sensing system with and without applying the enhancement of the invention. Random noise is less and drift is smaller. System reaches a stable condition in a shorter time. FIG. 4 shows the random noise of the enhanced system of this invention.

Figure 5A:
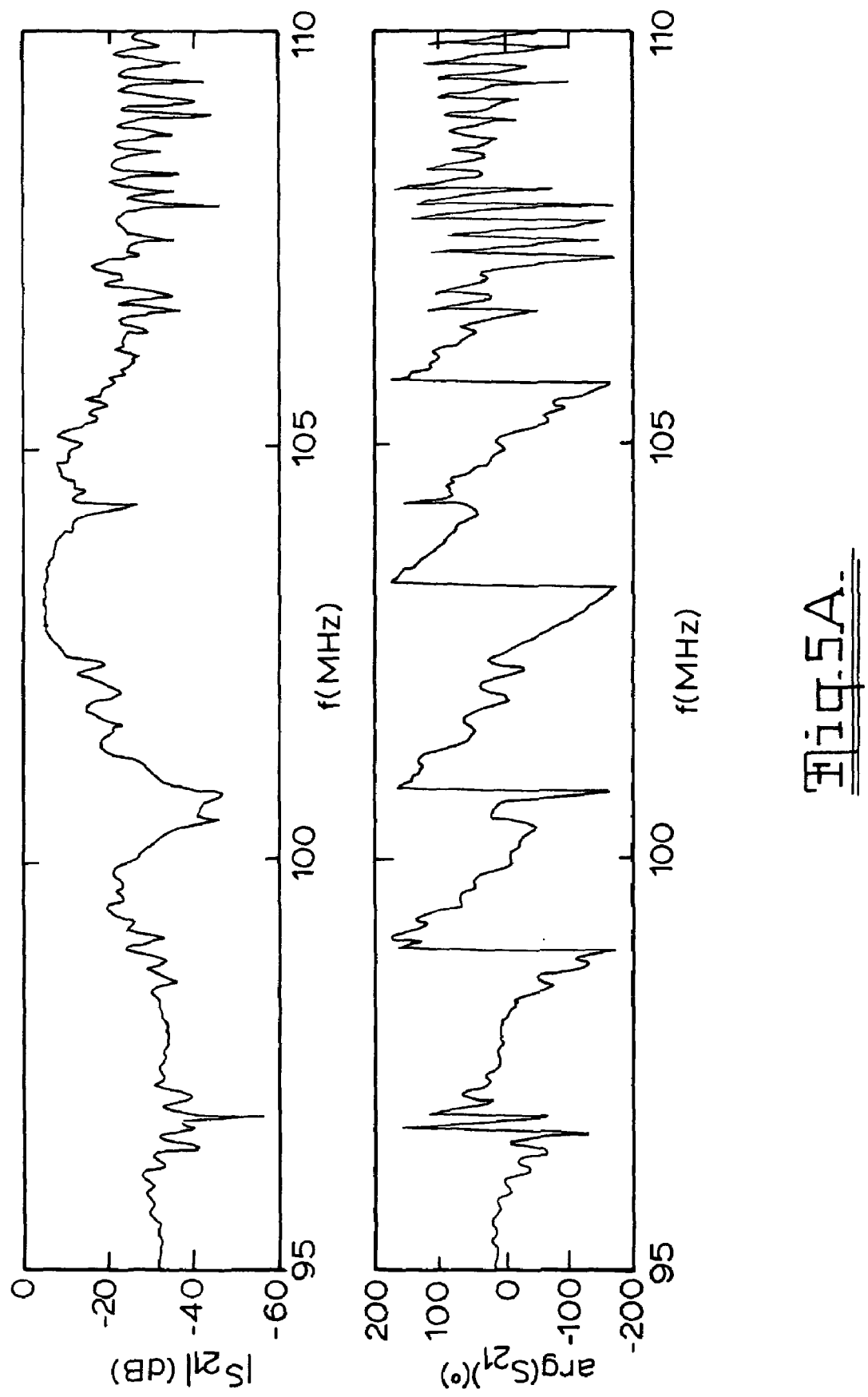
FIG. 5 illustrates the band width reduction achieved by the present invention.
Figure 5B:
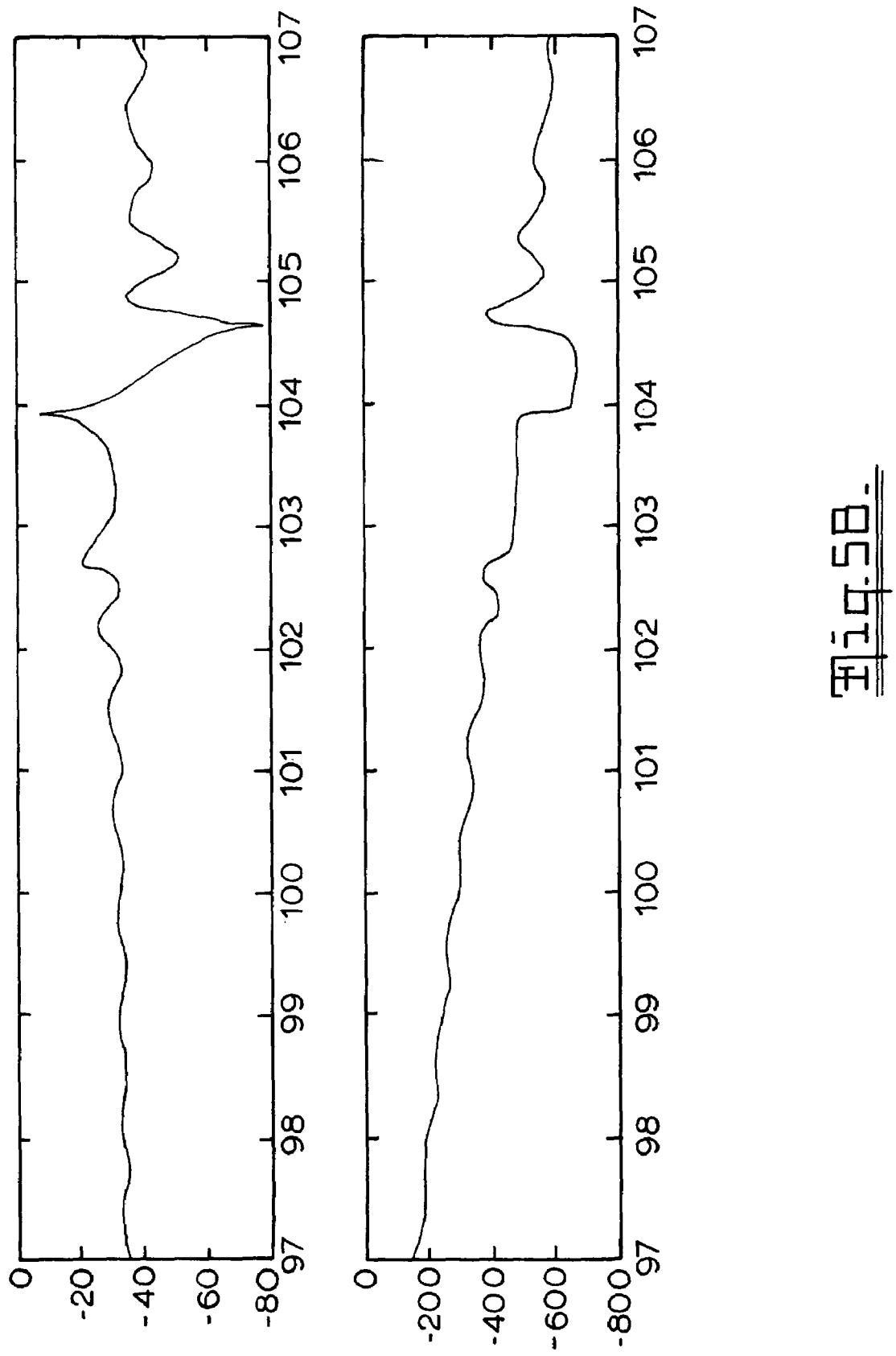

FIG. 5 illustrates the reduction of the bandwidth of a SAW device before and after introducing the changes. FIG. 5A shows the insertion loss of a SAW device before introducing the enhancements. FIG. 5B shows the insertion loss of a SAW device after introducing the enhancements. Bandwidth is at least 10 times smaller.

Figure 6:
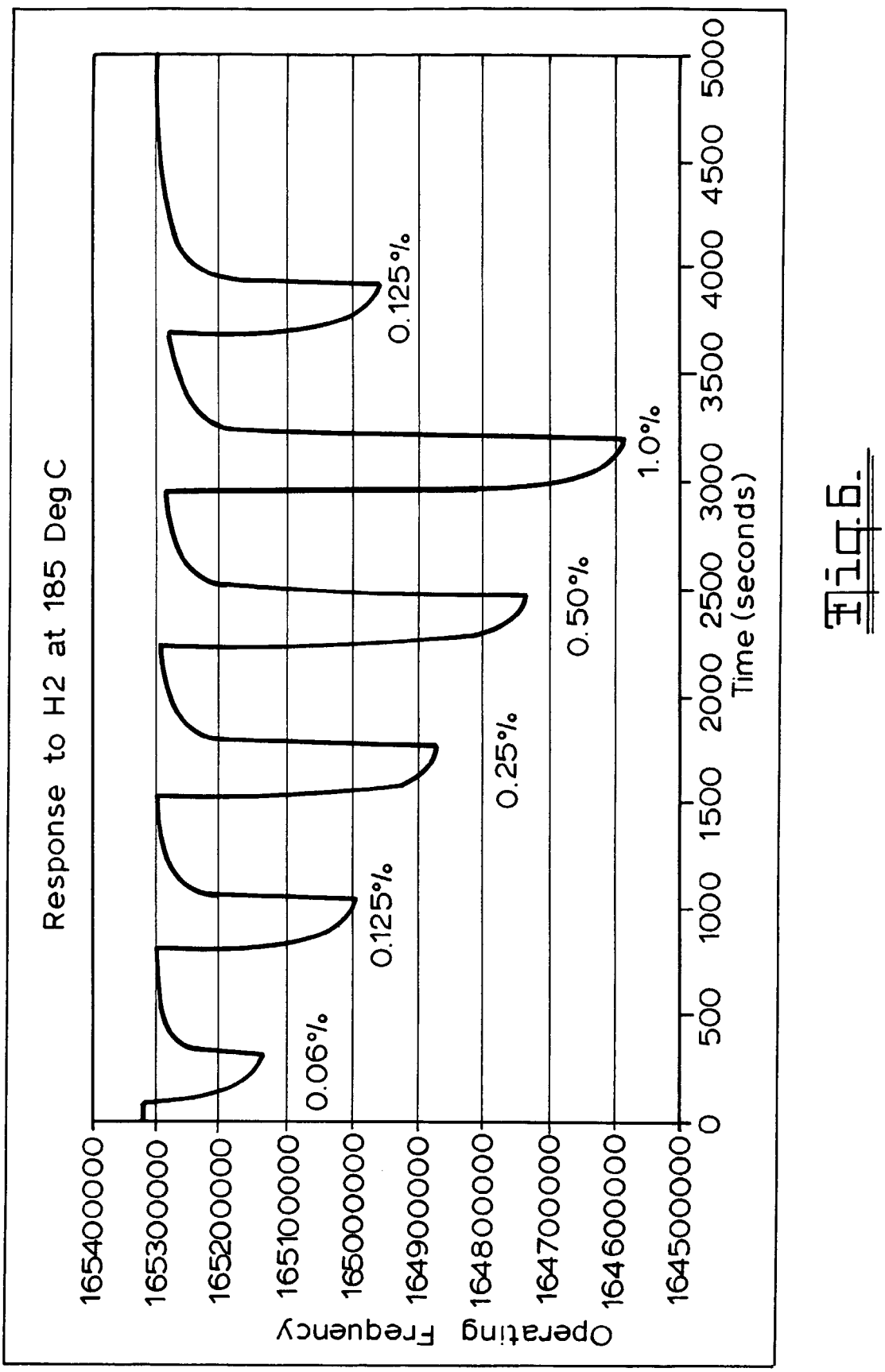
FIG. 6 illustrates the response of the sensor of this invention to hydrogen gas.

FIG. 6 illustrates the response of the layered SAW sensor (Structure: $LiTaO_3/ZnO/WO_3/Au$) to hydrogen gas.

Figure 7:
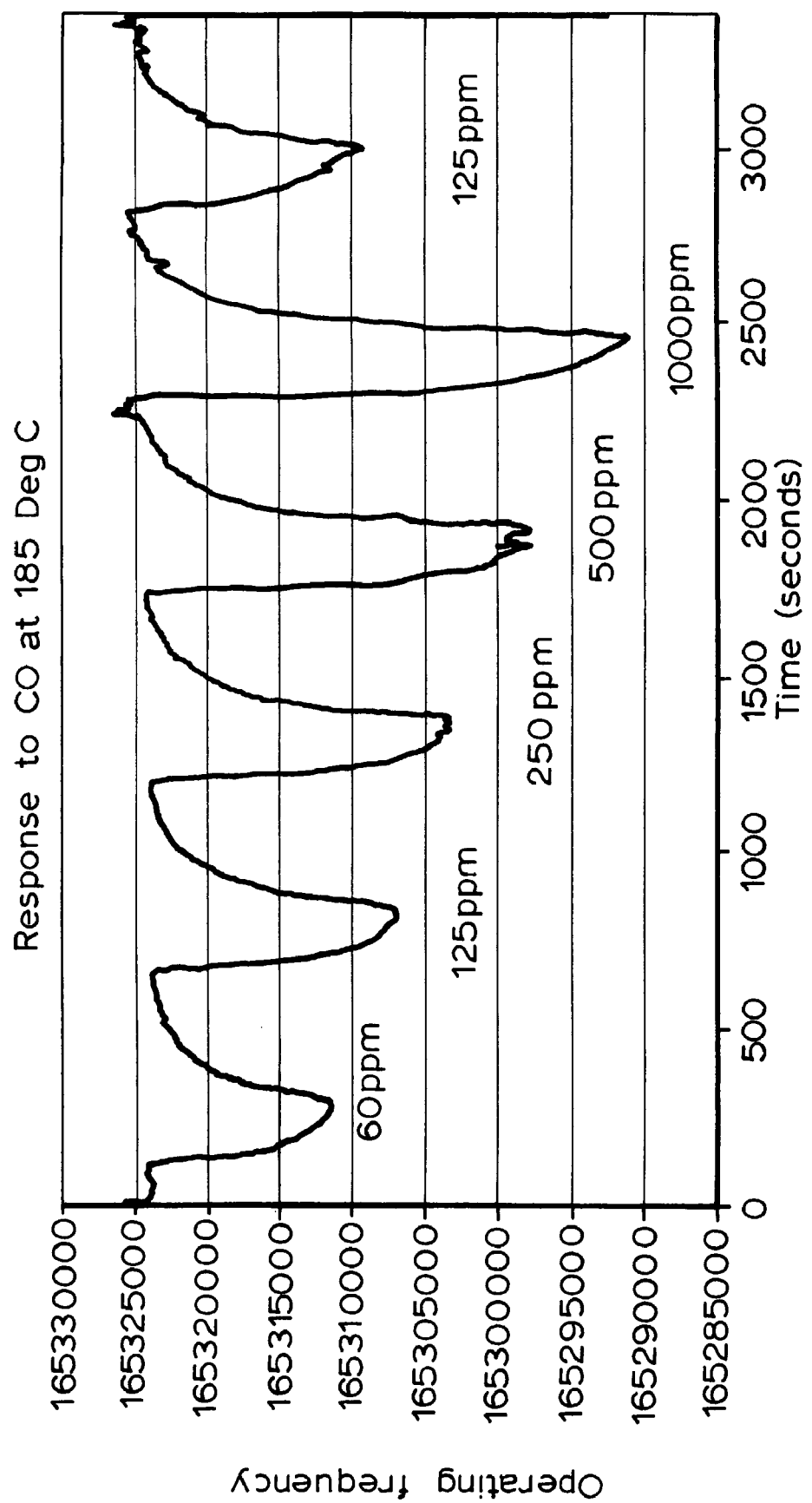
FIG. 7 illustrates the response of the sensor of this invention to carbon monoxide gas.

FIG. 7 illustrates the response of the layered SAW sensor (Structure: $LiTaO_3/ZnO/WO_3/Au$) to CO gas.

Figure 8:
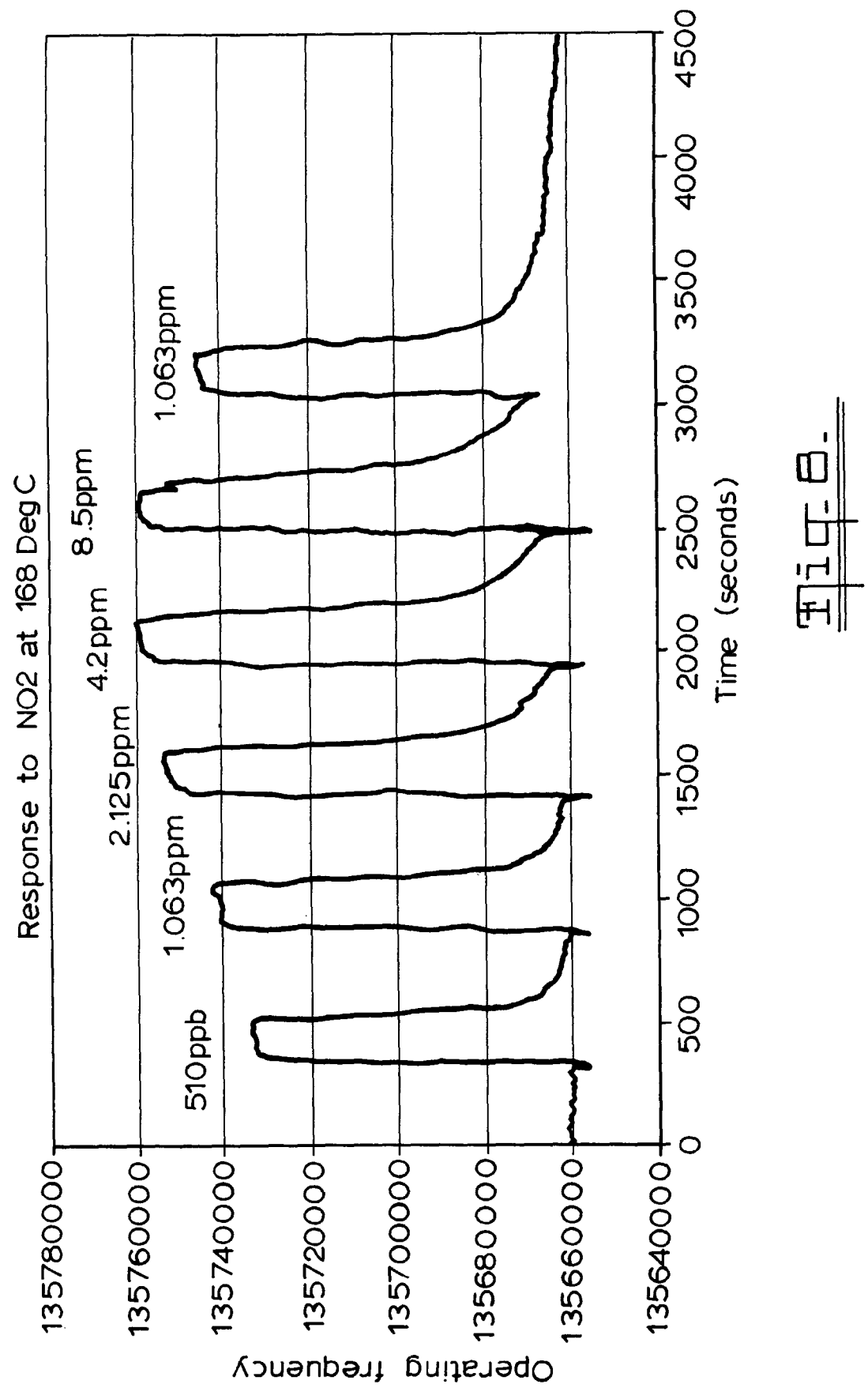
FIG. 8 illustrates the response of the sensor of this invention to nitrogen dioxide gas.

FIG. 8 illustrates the response of the layered SAW sensor (Structure: $LiNbO_3/ZnO/InO_x$ (20 nm)) to $NO_2$ gas.

Figure 9:
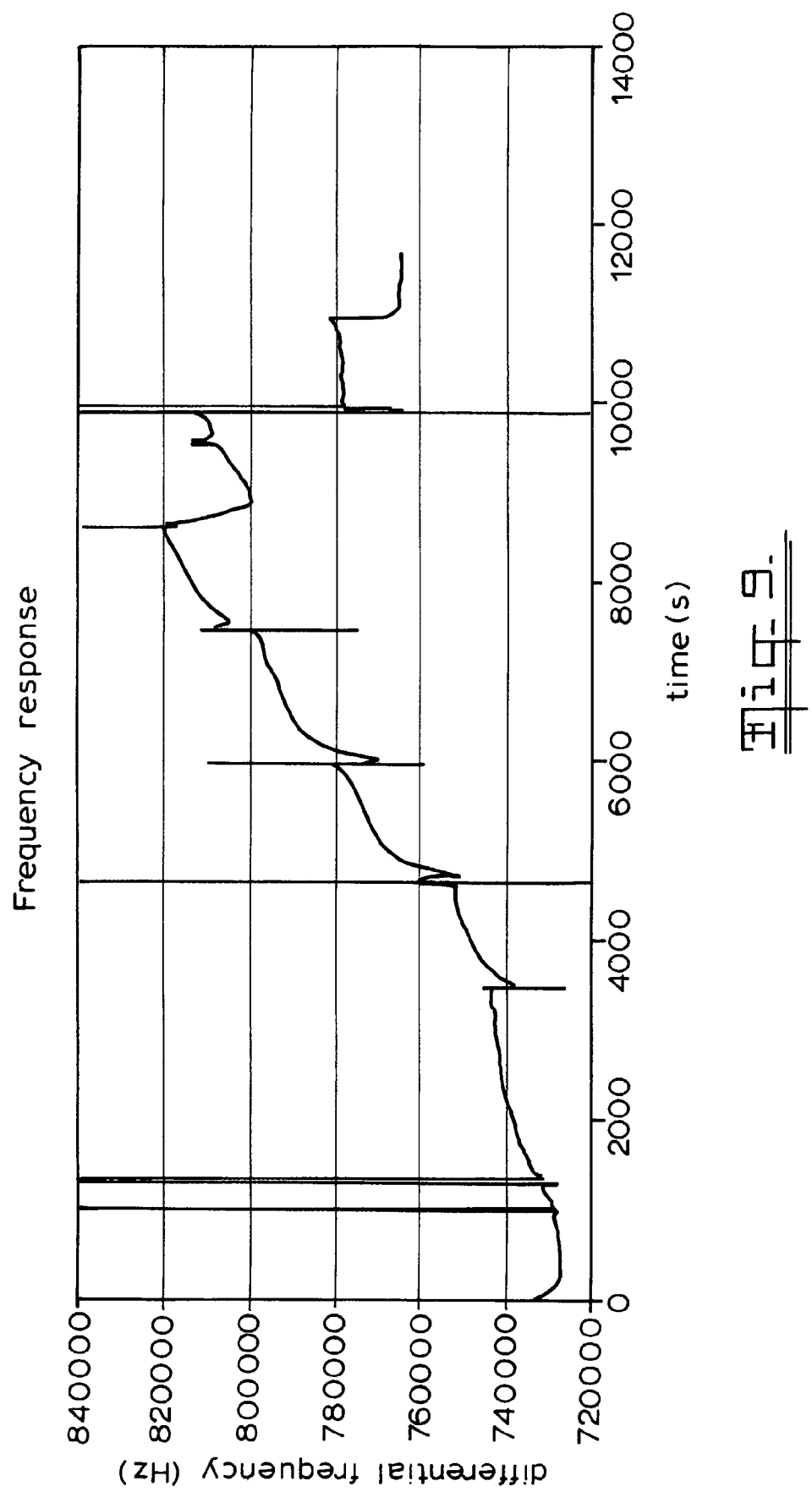
FIG. 9 illustrates the response of the sensor of this invention to biochemicals in a liquid.

FIG. 9 illustrates the response of the sensor of this invention to biochemicals in a liquid. The system shows a freq response linear to mass addition of the analyte in the solution for masses less than 500 ng for IgNAR. 100 ng, 200 ng, 200 ng and 500 ng of IgNAR has been introduced to the cell and then thoroughly washed.

COMPARATIVE EXAMPLES

Passive layers such as $SiO_2$ thin films are inefficient on 36 $LiTaO_3$ and Piezoelectric thin films such as ZnO have a better performance.

To show the mass sensitivity for $SiO_2$ layer different thicknesses of $SiO_2$ layers were deposited. The frequency shifts were measured.

Figure 10:
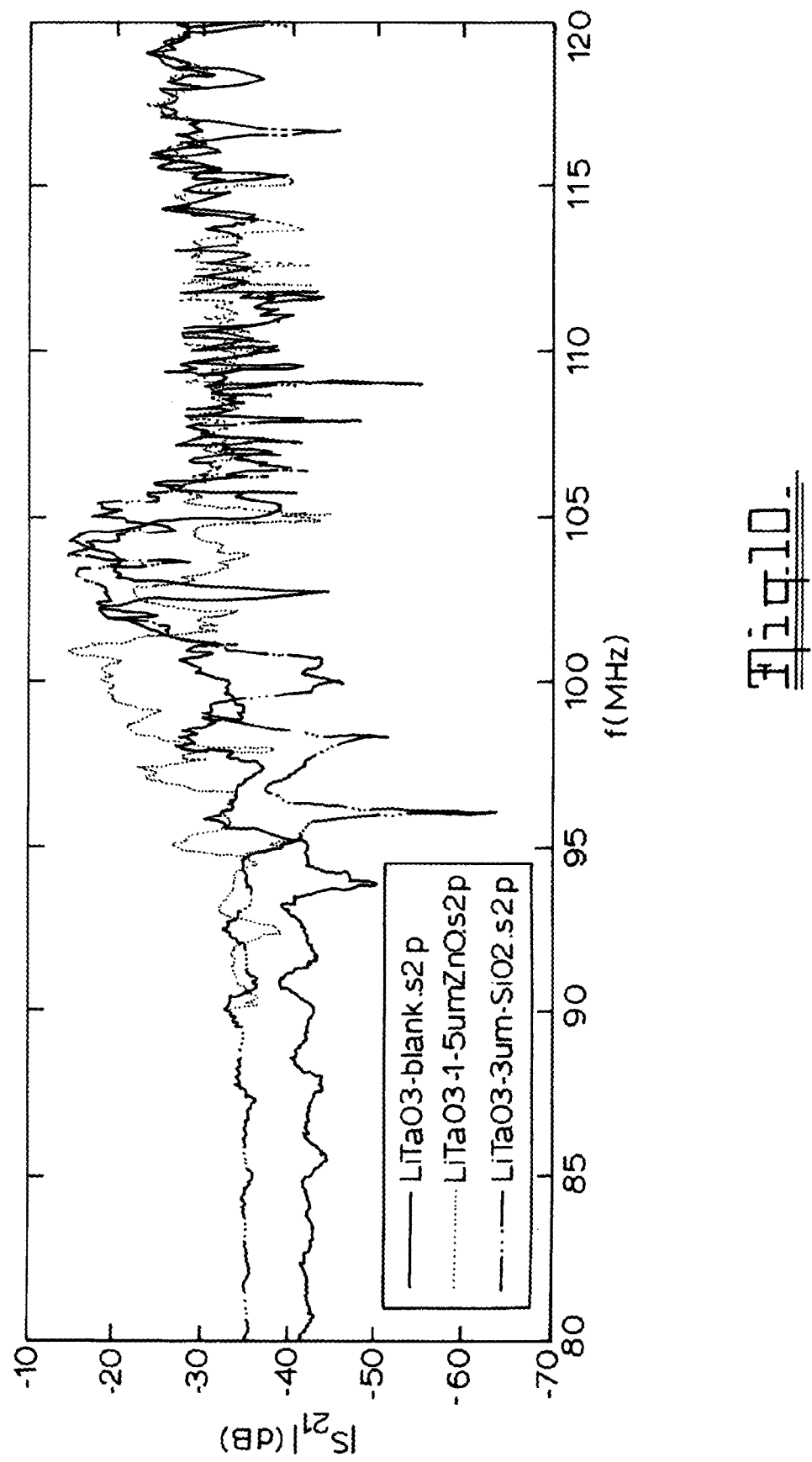
FIG. 10 illustrates the effect of ZnO SiO$_2$ layers on frequency shift.

On an approximately 100 MHz device the frequency shift is only 600 kHz for each µm of $SiO_2$ as shown in FIG. 10

As can be seen in FIG. 10 the frequency shift for a 1.5 µm ZnO/36 $LiTaO_3$ device is approximately 3 MHz but for a 3 µm $SiO_2$ devices is approximately 1.2 MHz.

The frequency shift for a 1.5 µm $SiO_2$ device is approximately 900 kHz

According to the measurements the ZnO/36 $LiTaO_3$ device is between 2.5 to 6 times more mass sensitive than $SiO_2$/36 $LiTaO_3$ device depending on the layer thickness and the type of mass added.

Mass sensitivity comparison between ZnO/64° $LiNbO_3$ and ZnO/36° $LiTaO_3$ as two typical substrates for the fabrication of layered SAW devices have been presented.

Figure 11:
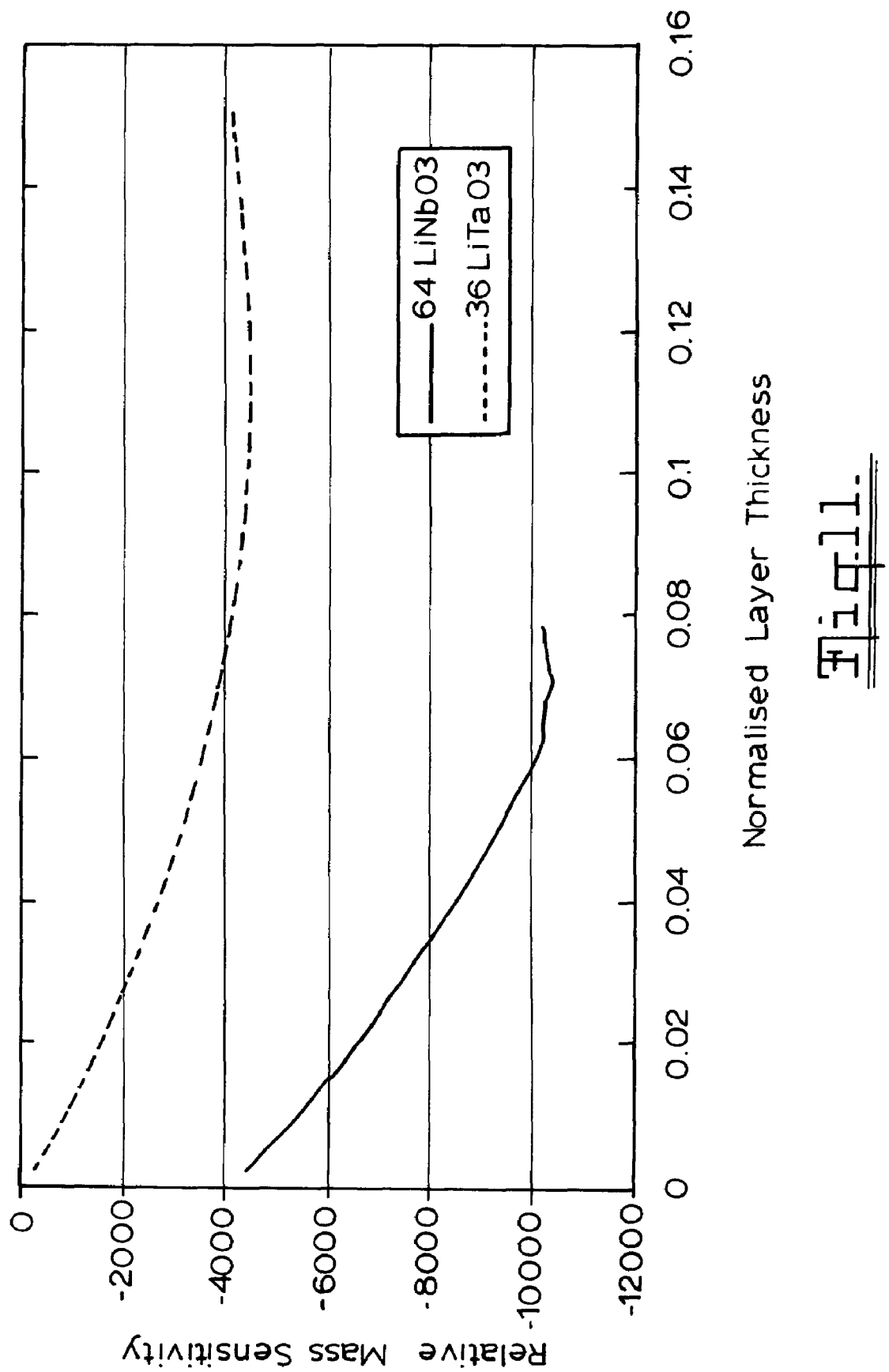
FIG. 11 illustrates the mass sensitivity of layered SAW devices based on 36 LiTaO$_3$ and 64 LiNbO$_3$ with ZnO guiding layers.

As can be seen in FIG. 11, the thickness for obtaining the optimum mass sensitivity for 64° $LiNbO_3$ is less than 36°$LiTaO_3$. At this optimum thickness, the 64° $LiNbO_3$ is about 2.5 times more mass sensitive.

Figure 12:
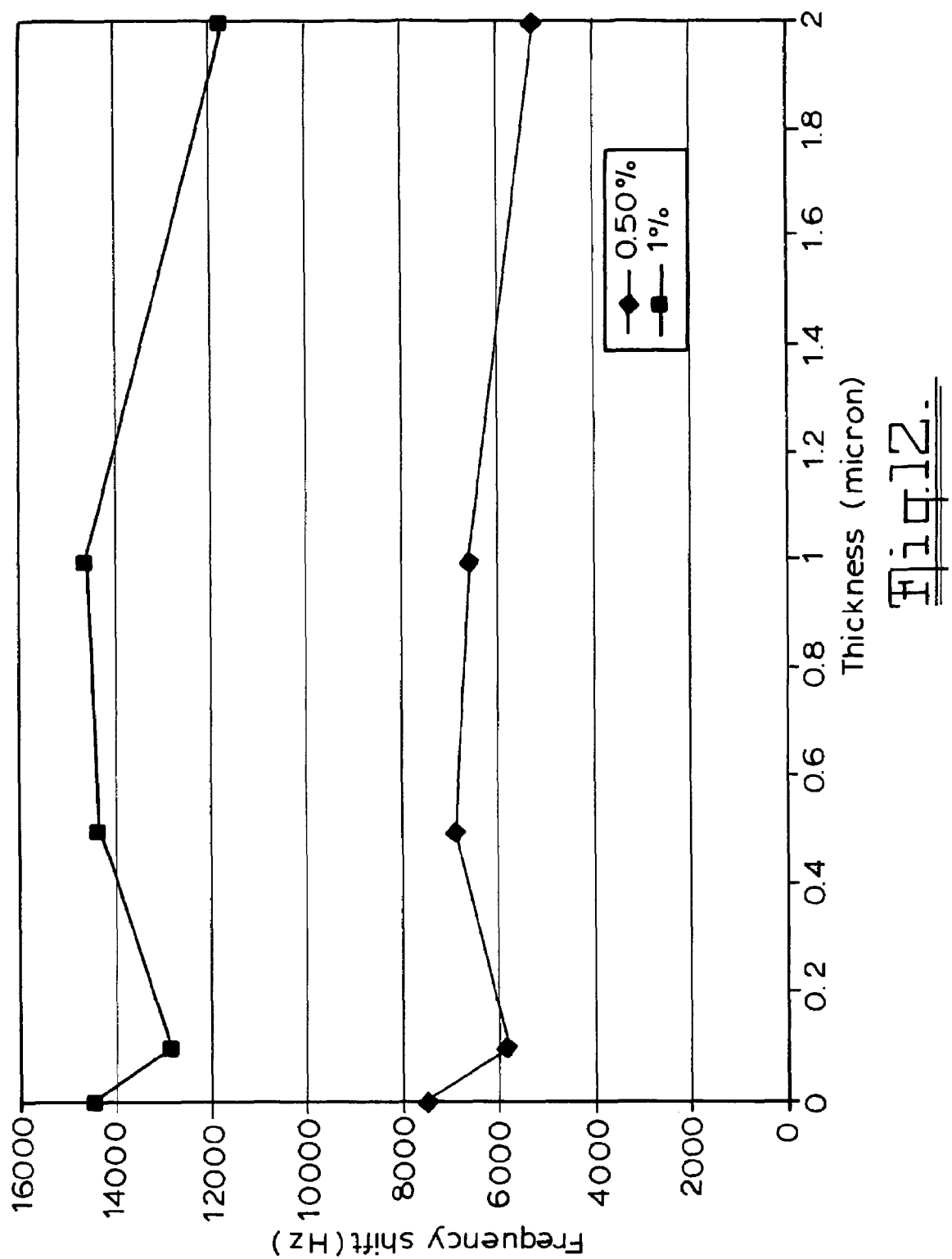
FIG. 12 illustrates the effect of conductivity change vs layer thickness.

The advantages of 64° $LiNbO_3$ over 36° $LiTaO_3$ are:
1—ZnO layer is smaller
2—Mass sensitivity is larger
3—It can be fabricated on a smaller wafer area as the piezoelectric constant coefficient is larger and makes the structure smaller However the temperature coefficient of frequency is larger for $LiNbO_3$. The ZnO layer on both sides has to have the exact thickness to eliminate the effect of temperature change The effect of conductivity change vs. the thickness of layer is shown in FIG. 12 Substrate 36 $LiTaO_3$ and layer is ZnO. $WO_3$ has been used as the selective layer to $H_2$ gas. 0.5% and 1% $H_2$ gas in air has been used in the measurements.

Magnitude of frequency shift vs ZnO thickness when exposed to $H_2$. The device structure is ZnO/36 $LiTaO_3$. The operational frequency is approximately 200 MHz.

FIG. 12 shows that the thickness of the layer has a significant effect on the conductivity and charge response of the device. Although this example is for gas sensing, the results are also applicable for the surface conductivity change which may occur in bio-sensing applications. The response in a bio-sensing situation will be some unknown combination of mass and conductivity contributions.

Those skilled in the art will realise that variations and modifications may be made to the invention as described without departing from the core teachings of the invention.

The invention claimed is:

1. A biological sensor which incorporates
   a) a first layered SAW device consisting of a piezoelectric crystal with interdigital electrodes on its surface, and second piezoelectric layer, of a different material to said piezoelectric crystal, over said interdigital electrodes
   b) a second layered SAW device consisting of a piezoelectric crystal with interdigital electrodes on its surface, a second piezoelectric layer, of a different material to said piezoelectric crystal over said interdigital electrodes and an analyte sensitive surface on said second piezoelectric layer
   c) both saw devices are fabricated on the same substrate and have an appropriate cavity length and aperture size
   d) the resonator circuits of each saw sensor incorporate amplifiers which are dependent.

2. A biological sensor as claimed in claim 1 in which an acoustically sensitive transitional layer lies between the piezoelectric crystal and the second piezoelectric layer.

3. A biological sensor as claimed in claim 1 or 2 in which the piezoelectric crystal is Lithium, Niobate or Lithium Tantalate and the second piezoelectric layer is zinc oxide.

4. A biological sensor as claimed in claim 3 in which the analyte sensitive surface is gold.

5. A biological sensor as claimed in claim 3 in which the cavity length of the two SAW devices is not less than 90° of the center to center distance of the two devices.

6. A biological sensor as claimed in claims 1 or 2 in which the aperture size is approximately 200 wavelengths.

7. A biological sensor as claimed in claim 1 in which the SAW devices include grooved gratings.

* * * * *